(12) United States Patent
Hickmott et al.

(10) Patent No.: US 11,738,169 B2
(45) Date of Patent: *Aug. 29, 2023

(54) URINARY CATHETER ASSEMBLY HAVING A SLEEVE ATTACHED BETWEEN A CONNECTOR AND A HANDLE

(71) Applicant: Coloplast A/S, Humlebaek (DK)

(72) Inventors: Richard Morgan Hickmott, Helsingoer (DK); Martin Wraber, Copenhagen OE (DK); Marie Bay Borg, Broenshoej (DK)

(73) Assignee: Coloplast A/S, Humlebaek (DK)

( * ) Notice: Subject to any disclaimer, the term of this patent is extended or adjusted under 35 U.S.C. 154(b) by 286 days.

This patent is subject to a terminal disclaimer.

(21) Appl. No.: 16/934,023

(22) Filed: Jul. 21, 2020

(65) Prior Publication Data

US 2020/0345977 A1 Nov. 5, 2020

Related U.S. Application Data

(63) Continuation of application No. 15/736,783, filed as application No. PCT/DK2016/050222 on Jun. 24, 2016, now Pat. No. 10,758,704.

(30) Foreign Application Priority Data

| Jun. 26, 2015 | (DK) | PA 2015 70396 |
| Jun. 26, 2015 | (DK) | PA 2015 70397 |
| Oct. 9, 2015 | (DK) | PA 2015 70643 |
| May 11, 2016 | (DK) | PA 2016 70313 |

(51) Int. Cl.
*A61M 25/00* (2006.01)
*A61M 25/01* (2006.01)

(52) U.S. Cl.
CPC ...... *A61M 25/0017* (2013.01); *A61M 25/002* (2013.01); *A61M 25/0097* (2013.01); *A61M 25/0111* (2013.01)

(58) Field of Classification Search
CPC .......... A61M 25/0111; A61M 25/0017; A61M 25/0097; A61M 39/12; A61M 25/002; A61M 39/10; A61M 2039/062; A61M 2039/1033; A61M 2210/1085; A61M 25/0014; A61M 39/1011; A61M 39/26; A61M 2025/0681; A61M 2039/1027;
(Continued)

(56) References Cited

U.S. PATENT DOCUMENTS

| 3,321,097 A | 5/1967 | Solowey |
| 3,967,728 A | 7/1976 | Gordon et al. |

(Continued)

FOREIGN PATENT DOCUMENTS

| CN | 1718940 A | 1/2006 |
| CN | 101132826 A | 2/2008 |

(Continued)

*Primary Examiner* — Adam Marcetich
(74) *Attorney, Agent, or Firm* — Coloplast Corp., Coloplast A/S; Nick Baumann

(57) ABSTRACT

A urinary catheter assembly includes an intermittent urinary catheter disposed in a cavity formed by a handle, and a connector, and a sleeve attached between the handle and the connector. The connector has a drain. The drain is formed by an outer wall of the connector separated from an inner wall of the connector by a channel.

12 Claims, 5 Drawing Sheets

(58) Field of Classification Search
CPC ...... A61M 2210/1089; A61M 25/0009; A61M 39/14; A61B 1/00154; A61B 17/3421; F16L 33/227; F16L 31/00; F16L 33/2076; F16L 35/00

See application file for complete search history.

(56) References Cited

U.S. PATENT DOCUMENTS

| | | | | |
|---|---|---|---|---|
| 4,168,699 | A | * | 9/1979 | Hauser ............ A61M 25/002 600/581 |
| 4,170,996 | A | * | 10/1979 | Wu ............ A61M 25/002 604/171 |
| 5,645,048 | A | * | 7/1997 | Brodsky ............ A61M 16/0841 128/207.14 |
| 6,045,542 | A | | 4/2000 | Cawood |
| 6,073,759 | A | | 6/2000 | Lamborne et al. |
| 10,758,704 | B2 | | 9/2020 | Hickmott et al. |
| 2001/0001443 | A1 | * | 5/2001 | Kayerod ............ A61M 25/002 206/364 |
| 2002/0144920 | A1 | * | 10/2002 | Samuels ............ B65H 75/364 206/364 |
| 2002/0151834 | A1 | * | 10/2002 | Utterberg ............ A61M 1/3643 604/4.01 |
| 2002/0193762 | A1 | | 12/2002 | Suydam |
| 2003/0060807 | A1 | | 3/2003 | Tanghoj et al. |
| 2005/0061698 | A1 | * | 3/2005 | Delaney ............ A61M 25/002 206/364 |
| 2006/0111681 | A1 | | 5/2006 | Vernon |
| 2006/0196783 | A1 | | 9/2006 | Bruun et al. |
| 2008/0172016 | A1 | | 7/2008 | House |
| 2009/0208368 | A1 | | 8/2009 | Waldrep et al. |
| 2011/0160662 | A1 | * | 6/2011 | Stout ............ A61M 25/0606 604/122 |
| 2011/0251572 | A1 | | 10/2011 | Nishtala et al. |
| 2011/0295239 | A1 | | 12/2011 | Gustavsson |
| 2012/0165790 | A1 | | 6/2012 | Gustavsson et al. |
| 2013/0161208 | A1 | | 6/2013 | Gustavsson |
| 2013/0186778 | A1 | | 7/2013 | Terry |
| 2013/0261607 | A1 | | 10/2013 | Nielsen |
| 2013/0261608 | A1 | | 10/2013 | Tanghoj |
| 2013/0292286 | A1 | | 11/2013 | Van Groningen et al. |
| 2013/0327664 | A1 | | 12/2013 | Tanghoj |
| 2013/0338615 | A1 | | 12/2013 | Zeller |
| 2014/0194842 | A1 | | 7/2014 | Schertiger et al. |
| 2015/0133898 | A1 | | 5/2015 | Murray et al. |
| 2015/0202421 | A1 | * | 7/2015 | Ma ............ A61M 39/22 604/167.03 |
| 2015/0250656 | A1 | | 9/2015 | Maksimow |
| 2016/0038713 | A1 | | 2/2016 | Kearns et al. |
| 2016/0038717 | A1 | | 2/2016 | Murray et al. |
| 2016/0193447 | A1 | | 7/2016 | Matthiassen |
| 2017/0000978 | A1 | | 1/2017 | Murray et al. |
| 2017/0203910 | A1 | | 7/2017 | Buse et al. |
| 2020/0222659 | A1 | | 7/2020 | Schertiger et al. |
| 2021/0290895 | A1 | | 9/2021 | Nielsen et al. |

FOREIGN PATENT DOCUMENTS

| | | | | |
|---|---|---|---|---|
| CN | 101803968 | A | | 8/2010 |
| CN | 202173621 | U | | 3/2012 |
| CN | 102654224 | A | | 9/2012 |
| CN | 102892452 | A | | 1/2013 |
| CN | 103127597 | A | | 6/2013 |
| CN | 103301551 | A | | 9/2013 |
| CN | 103791132 | A | | 5/2014 |
| CN | 103945893 | A | | 7/2014 |
| CN | 204840604 | U | | 12/2015 |
| EP | 1018323 | A1 | | 7/2000 |
| EP | 2072075 | A1 | | 6/2009 |
| EP | 2695636 | A1 | | 2/2014 |
| GB | 2007507 | A | * | 5/1979 ......... A61M 25/002 |
| JP | 2014023605 | A | | 2/2014 |
| RU | 2013130998 | A | | 1/2015 |
| RU | 2013131785 | A | | 1/2015 |
| RU | 2584649 | C2 | | 5/2016 |
| RU | 2598811 | C2 | | 9/2016 |
| WO | 2000016843 | A1 | | 3/2000 |
| WO | 2009152609 | A1 | | 12/2009 |
| WO | 2013029620 | A1 | | 3/2013 |
| WO | 2018059637 | A1 | | 4/2018 |
| WO | 2020015804 | A1 | | 1/2020 |

* cited by examiner

URINARY CATHETER ASSEMBLY HAVING A SLEEVE ATTACHED BETWEEN A CONNECTOR AND A HANDLE

The invention relates to a urinary catheter assembly comprising a sleeve.

SUMMARY OF THE INVENTION

The invention relates to a urinary catheter assembly comprising a urinary catheter having a hydrophilic surface. The urinary catheter is provided with a tip portion in a proximal end of the urinary catheter and an outlet at a distal end of the urinary catheter. A handle is slidingly disposed on the urinary catheter, and a collapsible, flexible sleeve is attached to the handle and is configured to cover the urinary catheter from the outlet to the insertion tip in an extended configuration. The sleeve is attached to a connector at the outlet, the connector and handle are configured to be attached to each other in a detachable manner, so that in the storage condition when the connector and handle are attached to each other, the urinary catheter is encapsulated completely inside a cavity provided by the sleeve, handle and connector.

BRIEF DESCRIPTION OF THE DRAWING

The accompanying drawings are included to provide a further understanding of embodiments and are incorporated into and are a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION OF THE INVENTION

Figure 1:
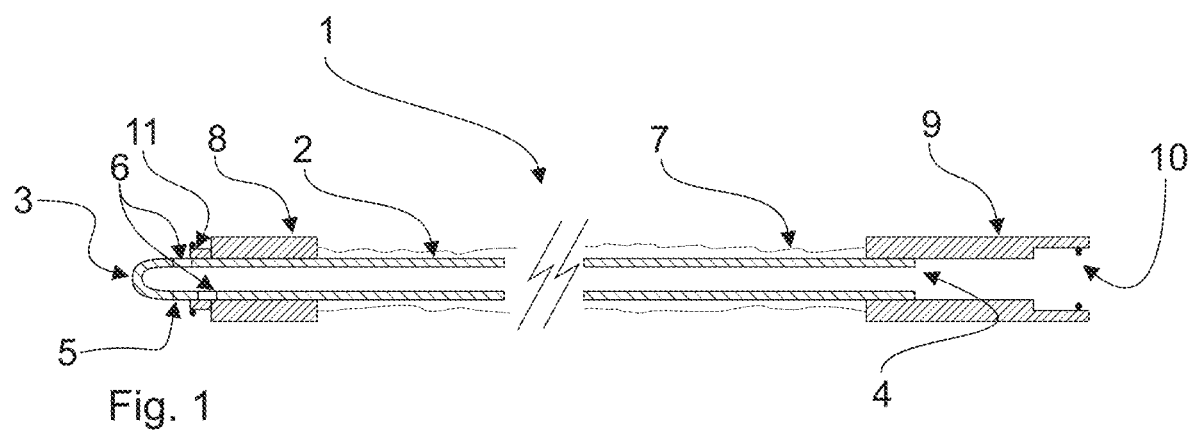
FIG. 1 illustrates an embodiment of the urinary catheter assembly in a configuration, where it is ready to be used.

Urinary catheter assemblies for draining the bladder are increasingly used for intermittent as well as indwelling or permanent catheterisation. Typically, urinary catheters are used by patients suffering from urinary incontinence or by disabled individuals like paraplegics or tetraplegics, who may have no control permitting voluntary urination and for whom catheterisation may be the way of urinating.

Urinary catheters are divided into two major groups of catheters, indwelling catheters and intermittent catheters. Indwelling catheters are typically inserted into the urethra and the bladder by medical personal (i.e. a trained professional, typically a nurse or physician) and has means for retaining the catheter inside the bladder for up to two weeks or more. Indwelling catheters are soft and flexible since they have to remain in the urethra for weeks. Indwelling catheters empty the bladder continuously.

Intermittent catheters are typically inserted by the user him- or herself and sits only in the urethra and bladder for as long as it takes to empty the bladder—e.g. for about 5-10 minutes. Intermittent catheters are used every 4-6 hours to empty the bladder corresponding roughly to the interval with which people having no urinary problems will usually go to the bathroom. Intermittent catheters are typically more rigid than indwelling catheters since they have to be inserted by the user him-/herself and since they do not need to sit in the urethra for days or weeks. An important feature for the intermittent catheter is to ease the insertion into the urethra. This is done by providing the intermittent catheter with a low frictious surface. A low friction surface may be obtained by providing the intermittent urinary catheters with a hydrophilic coating that needs to be wetted prior to use and thereby absorbs a considerable amount of liquid. Such a hydrophilic coating will provide a very lubricious surface that has very low-friction when the catheter is to be inserted. Hydrophilic coated catheters, where the coating absorbs a considerable amount of liquid for a low frictious surface (swelling degree >100%), will not be suitable for indwelling catheters, because the hydrophilic surface coating would stick inside the mucosa of the urethra if left inside the body for a longer period of time, due to the hydrophilic coating transforming from being highly lubricious when fully wetted to being adhesive when the hydration level of the coating is reduced.

The urinary catheter as described above is configured to be used intermittently and is provided with a hydrophilic surface.

Embodiments relate to a urinary catheter assembly comprising a urinary catheter having a hydrophilic surface, the urinary catheter being provided with an insertion tip in a proximal end of the urinary catheter and an outlet at a distal end of the urinary catheter, a handle being slidingly disposed on the urinary catheter, a collapsible, flexible sleeve attached to the handle and being configured to cover the urinary catheter from the outlet to the insertion tip in an extended configuration, the sleeve being attached to a connector at the outlet, the connector and handle being configured to be attached to each other in a detachable manner, so that when the connector and handle are attached to each other, the urinary catheter is encapsulated completely inside a cavity provided by the sleeve, handle and connector.

By being configured to cover the urinary catheter from the outlet to the insertion tip is meant that the sleeve covers a majority of the longitudinal extent of the catheter in an extended configuration. The connector and handle are typically attached to each other in a storage condition, and in that storage condition, the urinary catheter is encapsulated completely inside the cavity provided by the sleeve, handle and connector. In a use condition or extended configuration of the assembly, the connector and handle are detached from each other and, typically, the liquid will be drained out from the cavity. The storage condition may also be known as the closed configuration of the urinary catheter assembly and the use condition may be known as the open configuration of the urinary catheter assembly.

One advantage of the urinary catheter assembly is that the sleeve, connector and handle provide a complete enclosure (a cavity) for the urinary catheter, so that in the storage condition, the sterility is not compromised in any way—even as the catheter assembly is removed from an optional storage package. The user may drop the assembly on the floor or even into the toilet, without compromising the sterility of the urinary catheter itself. In particular, the insertion tip is protected from being contaminated by contact with anything unclean as long as the connector is connected to the handle. Furthermore, when the urinary catheter is to be used, the user simply detaches the connector from the handle. Following unfolding or unrolling of the urinary catheter assembly, the urinary catheter is ready to be used. The sleeve further provides the user with the possibility of gripping and holding the urinary catheter so that it is easier to use. Thereby, the catheter itself can be made of a softer and more bendable material than a catheter that is to be inserted in a straight position.

In a urinary catheter assembly as described above, the user of the assembly only has to handle one item. Users of urinary catheter assemblies may have reduced hand dexterity making it difficult for them to handle several items. Therefore, it may be an advantage that no extra items (e.g. caps or closures) need to be handled. Furthermore, when the connector and handle are separated, each of these two parts provides an intuitive location for handling the catheter, which can be done without compromising the sterility of any part of the catheter.

In the following, whenever referring to a proximal end of an element of the invention, the referral is to the end adapted for insertion. Whenever referring to the distal end of an element, the referral is to the end opposite the insertion end. In other words, the proximal end is the end closest to the user, when the catheter is to be inserted and the distal end is the opposite end—the end furthest away from the user when the catheter is to be inserted. The same definitions apply to the package and container—the proximal end is the end storing the proximal end of the catheter and the distal end is the opposite end.

The longitudinal direction is the direction from the distal to the proximal end. The transverse direction is the direction perpendicular to the longitudinal direction, which corresponds to the direction across a shaft of the catheter.

The urinary catheter comprises a main tubular part extending from the distal end to the proximal end. The tip portion is positioned at a proximal end of the catheter and comprises an eyelet part with eyelets and a proximal part proximal of the eyelet part. The proximal part may comprise a proximal rounded closed end of the tubular part. The eyelets may serve the purpose of letting urine enter into the inner lumen of the tube. The tip portion may be a Nelaton tip, where the proximal end is simply closed off providing a half-spherical closed end. The tip portion may be integrally moulded with the main tubular part—either as 1 component or 2 component moulding—or it may be provided as a separate element and then attached to the main tubular part, e.g. by welding or adhering. The tip portion may also be made by modifying the main tubular part, i.e. by punching the eyelets and rounding the proximal end to close it off.

The urinary catheter may be made of a polyurethane material (PU) or polyvinyl chloride (PVC) or poly-olefins such as a polyethylene (PE).

Usually urinary catheters for intermittent use are from size 8 FR to size 18 FR. FR (or French size or Charriere (Ch)) is a standard gauge for catheters approximately corresponding to the outer circumference in mm. More accurately, the outer diameter of the catheter in mm corresponds to FR divided by 3. Thus, 8 FR corresponds to a catheter with an outer diameter of 2.7 mm and 18 FR corresponds to a catheter with an outer diameter of 6 mm.

Urinary catheters of this invention has a hydrophilic surface imparting a low-friction insertion and may prior to use be provided with a hydrophilic coating.

The hydrophilic coating may be provided only on the insertable part of the catheter. The hydrophilic surface coating is of the kind which, when hydrated or swelled using a swelling medium, reduces the friction on the surface area of the catheter which is intended to be inserted into the urinary channel of a user corresponding to the insertable part of the catheter.

An intermittent hydrophilic catheter differs from an indwelling catheter in that the hydrophilic surface coating of such a catheter is not suitable for indwelling use, because the surface coating tends to stick inside the mucosa of the urethra if left inside the body for a period exceeding 5-20 minutes, due to the hydrophilic coating transforming from being highly lubricious when fully wetted (95% weight water) to being adhesive when the hydration level of the coating is reduced (<75% weight water).

In the storage condition, the urinary catheter assembly comprises a medium for activating the hydrophilic surface coating of the catheter. The activating medium may be a water based substance, such as sterile water, or a saline-solution.

In an embodiment, the catheter is a male catheter meaning that the catheter has an insertion length of at least 250 mm, more preferred at least 300 mm.

At its proximal end, the sleeve is connected to the handle. In the distal end, the sleeve is connected to the connector. This ensures that the entire catheter is protected from being contaminated by bacteria from the exterior.

In an embodiment, the connector and handle are provided with interlocking means.

In an embodiment, the interlocking means are in form of a threaded coupling. The thread may be short so that the user only has to turn the handle and connector about 90 degrees or even less, such as 60 degrees, to disconnect the handle and connector from each other. The threaded coupling has the advantage that it is easy to use even for users having poor hand dexterity.

In an embodiment, a kit of parts is provided with a catheter assembly as mentioned above in combination with a urine collecting bag and a tube connecting the urine collecting bag with the connector on the catheter assembly. The catheter assembly may be provided with interlocking means in the form of a threaded coupling and the tube may be provided with a threaded coupling adapted for cooperation with the threaded coupling on the connector. Such a threaded coupling may be used to provide a secure connection between the catheter and the tube connecting a urine collecting bag to the catheter. Users may experience that a urine collecting bag coupled to a catheter may accidentally detach from the connection and as a result urine leaks out onto the clothes or on the floor. This drawback may be alleviated by using a threaded coupling in the connector and provide a urine collecting bag with a corresponding threaded coupling at the connecting tube.

In an embodiment, the interlocking means are provided as first snap-fit means on the connector and second snap-fit means on the handle, the first and second snap-fit means being complementary snap-fit means. This is an easy and well-functioning way of making the connector and handle detachably attached to each other. The snap-fitting means may be provided as an annular and radially inwardly extending ridge inside the connector adapted for cooperation with an annular groove on the outer surface of the handle. However, other means such as resilient vanes cooperating with grooves may be used.

The interlocking means between the connector and handle may, in some embodiments, allow for reclosing the urinary catheter assembly following use—as will be explained later. For example, a threaded coupling allows for opening as well as reclosing the sleeve. Likewise, a snap-fit coupling may also allow for opening as well as reclosing the sleeve. In other words, embodiments relate to a catheter assembly as described above wherein the sleeve is recloseable.

A recloseable product allows for a hygienic handling of the catheter throughout the entire procedure from removing it from the storage package to disposal of the product.

In an embodiment, the connector is configured to contain and protect the tip portion of the catheter.

The connector may be made of a rigid material, so that the insertion tip can be protected inside the connector, when the connector is connected to the handle. Thereby, in the storage condition, the urinary catheter assembly may be in the form of a ring-shaped assembly, completely contained inside the cavity provided by the sleeve, handle and connector. A flexible insertion tip portion, meaning a tip portion that is easily bendable, may be prone to permanent deformation during storage, unless it is ensured that the tip portion is prevented from being bent during storage. This is obtained by providing the connector of a relatively rigid material so that the storage cavity provides protection against bending for the tip portion.

In an embodiment, the sleeve is liquid tight and configured to store liquid in the cavity provided by the sleeve, handle and connector. This means that the swelling medium or activating medium needed for the hydrophilic coating can be contained inside the sleeve so that the hydrophilic surface on the catheter is activated by the liquid. The material for the sleeve may, for example, be a foil-material of polyethylene, such as a soft polyethylene of LDPE. The material may also be an ethylene based plastomer. It is contemplated that materials having a flexural modulus of less than 300 MPa measured according to ISO 178 will be adequately collapsible. By adequately collapsible is meant that the sleeve provides only little resistance to being collapsed towards the distal end. Thus sleeve materials having a flexural modulus of less than 100 MPa may also be used. The sleeve provides an antimicrobial barrier.

One advantage of storing the liquid inside the cavity provided by the sleeve, handle and connector may be that the outer surface of the sleeve is dry.

Embodiments relate to a kit of parts comprising the assembly as described above and a storage package of a water vapour impermeable material. The storage package provides an enclosure for the urinary catheter assembly including the sleeve, handle, connector and urinary catheter.

By water vapour impermeable is meant that the material has such a low water vapour permeability that the urinary catheter assembly can be stored in the storage package with the coating being kept in a fully hydrated condition for a storage time of up to 3 years. As an example, the material for the storage package is a foil-package of a laminate including a thermoplastic material and aluminium, e.g. a laminate of a PETP polyester as an outer layer, aluminium in an intermediate layer and an inner layer of polyethylene. This foil-package may be provided in one sheet of material folded over and welded or adhered along the edges to provide an enclosure. It may also be provided in two sheets of material laid on top of one another and welded or adhered along the edges to provide an enclosure. As another example, the storage package is a hard-box injection moulded of Polypropylene or Poly-ethylene in a thickness of about 0.7 mm or more. This hard-box may be provided with a lid integrated with or separate from the remaining part of the hard-box and provides an enclosure inside it.

In an embodiment, a storage package of water vapour impermeable material includes a number of urinary catheter assemblies. As an example, the storage package includes 5-6 urinary catheter assemblies, so that the user has the number of catheters to be used in a day in one storage package. This is possible, because the sleeve includes the swelling medium and is able to store the urinary catheter in a hydrated or swelled condition for at least 24 hours. Thus, the storage package provides the water vapour impermeability needed for long-term storage (e.g. 3 years) and the sleeve provides water vapour impermeability needed for approximately a day or two.

The storage package may be recloseable, irrespective of whether the storage package is provided for storing one or more catheters. If the storage package is provided as a foil-package, it may be provided with a peelable opening and a resealabe tape allowing the storage package to be resealed over the opening. In case the storage package is provided as a hard-box, it may be resealed by reclosing the lid.

In an embodiment, the tip portion is a flex tip. In this type of embodiment, the tip portion of the urinary catheter comprises, from the distal end of the tip portion, an eyelet part with eyelets for letting urine into the inner lumen of the catheter, an intermediate part, where the catheter diameter is decreased with respect to the diameter of the remaining part of the catheter, and a proximal part having a bulb with a diameter close to or exceeding the diameter of the tubular part of the catheter. The bulb may also have a diameter that is slightly less than the diameter of the tubular part of the catheter. The bulb may be close to spherical in shape or may be slightly elongated and shaped as an olive or droplet. This type of tip portion may be useful for male users to guide the catheter around the bend in the urethra at the prostate. The urinary catheter assembly as described above allows the tip portion to be protected inside the connector without being bend. A flexible tip portion is adapted to bend easily—and because of the visco-elasticity of the material, the tip portion will have a tendency to deform permanently into a curved position if being subjected to bending for a prolonged period of time. This means that such a bend in the tip portion may be difficult, if not impossible to straighten out again, when the catheter is to be used. Thereby, the catheter will be difficult to insert during the straight part of the urethra.

The eyelets will influence the bending stiffness of the catheter in such a way that the eyelet part will have a reduced bending stiffness compared to the main tubular part of the catheter. The intermediate part may have a diameter that is decreased to such an extent that the bending stiffness of this part is between 60% and 80% of the bending stiffness of the main tubular part of the catheter. This reduced diameter and resulting reduced bending stiffness assist in preventing the catheter from kinking at the eyelets, because the deflection of the catheter will be more evenly distributed, when the intermediate part of the catheter is less rigid (has a lower bending stiffness) than the eyelet part.

In an embodiment, when the urinary catheter is straightened out, the sleeve does not completely cover the insertion tip, but up to 10 mm of the tip portion projects beyond the proximal end of the handle. This has the effect that the proximal end of the tip portion is immediately visible and accessible for insertion into the urethra, whereas the eyelet part with the eyelets will still be positioned inside the handle. Having the eyelets inside the protection of the handle is an advantage, because the catheter is more likely to kink at the eyelets than at other cross-sections along the length of the catheter. So the user can initiate insertion of the urinary catheter into the urethra and still support the eyelet part of the urinary catheter by squeezing the handle into contact with this part.

The handle may have a soft proximal end. A soft proximal end of the handle prevents irritation of the glans of a penis, should the handle come into contact with the glans, when catheterization is to be done. This may be done by providing the proximal end of the handle with a sealing ring, e.g. of thermoplastic elastomeric material (TPE). Another or additional way of doing this is to provide an entire outer surface of the handle with a soft material and provide an inner supporting part of Polypropylene (PP). In an embodiment, the handle has an outer surface of TPE and an inner supporting part of PP comprising the threaded surface. The handle may then be squeezed into contact with the catheter surface so that the catheter can be easily handled through the sleeve.

The connector may comprise an inner connector part and an outer connector part. This allows a standard inner connector to be used as an outlet, which allows connection to a urine bag. As an example, the inner connector may be made of polyurethane. The outer connector part may be made of Polyethylene, such as HDPE. In an embodiment, where the connector and handle are adapted for being threaded together, the outer connector part supports the thread, thus it is rigid enough to support the thread. The two connector parts may be configured to be friction-fitted, press-fitted or snap-fitted together.

Embodiments relate to a urinary catheter assembly, wherein the connector forms a drainage structure providing drainage of liquid (activating medium) from the cavity in the open configuration without providing drainage in the closed configuration.

In other words, when the connector and handle are detached from each other and the urinary catheter assembly is in the use condition, the liquid may be drained out from the assembly through a drainage structure in the connector, whereas the liquid is prevented from being drained out from the assembly in the storage condition. When the catheter is to be used, it is advantageous to handle and dispose of the liquid (typically around 15 ml) appropriately.

The urinary catheter assembly connector is capable of forming a closed configuration and an open configuration. In the closed configuration, the connector and handle can be attached to each other such that the urinary catheter is encapsulated completely in a cavity formed by the sleeve, handle, and connector. This is achieved by looping or coiling the assembly such that the connector and handle meet and can attach.

The connector forms a drainage structure which provides drainage of liquid from the cavity in the open configuration without providing drainage in the closed configuration. Typically, the drainage structure is a hole which extends through the connector and allows liquid drainage from the cavity in the open configuration. The drainage structure may be located in the interlocking means of said connector.

In a particular embodiment, the connector comprises an inner connector and an outer connector, said inner and outer connectors being separated by a channel for liquid, wherein said drainage structure is present in said inner connector. In this embodiment, the outer connector may comprise said interlocking means.

By means of the drainage structure, liquid in form of an activating medium can be drained from the distal end of the catheter. The activating medium may be drained into a toilet. The distal end of the catheter may be connected to a urine bag or hose for disposal, as described above.

Embodiments also relate to a method for preparing a urinary catheter for insertion, said method comprising the steps of:
providing the urinary catheter assembly in said closed configuration;
releasing the connector and handle from each other to form the open configuration;
draining liquid from the cavity through said drainage structure.

Embodiments relate to providing a catheter assembly as described above in a rolled-up configuration. By a rolled-up configuration is meant that the catheter is rolled in at least two convolutions. Providing a catheter in a rolled-up configuration during storage has the effect that the catheter is more compact during storage.

Embodiments include a kit of parts comprising a catheter with a standard connector and a sleeve with a connector part in the distal end adapted for being fitted, as mentioned above, to the standard connector of the catheter. The sleeve includes a handle as described above. The catheter may be provided with a hydrophilic coating as described above. The cooperation between the handle and the connector may be as described above.

The catheter assembly can advantageously be delivered to the user in a rolled-up configuration with the connector attached to the handle. When a user is about to use the catheter, he may initially remove the catheter enclosed in the sleeve from the storage package, in case a storage package is provided. The connector is the separated from the handle and the activating medium is drained out of the sleeve, in some embodiment through a drainage structure as described above. In some embodiments the sleeve is reclosable and the assembly can be kept in a bag or pocket for later disposal. In some embodiments, re-storing the catheter assembly in a storage package and re-sealing this is possible, as it is described above.

DETAILED DESCRIPTION OF THE DRAWING

Embodiments, and features of the various exemplary embodiments described in this application, may be combined with each other ("mixed and matched"), unless specifically noted otherwise.

FIG. 1 illustrates a cross-sectional view of an embodiment of a urinary catheter assembly 1, when it is ready to be used. The urinary catheter assembly 1 includes a urinary catheter 2, extending from a proximal insertion end 3 to a distal end comprising outlet 4. The proximal end 3 includes a tip portion 5 with eyelets 6 for letting urine enter into the catheter. The assembly 1 further includes a sleeve 7 extending between a handle 8 and a connector 9. The sleeve 7 is collapsible as the handle 8 is slid along the catheter 2, e.g. during insertion. The connector 9 includes a first snap-fit means 10 configured to cooperate with a complementary second snap-fit means 11 on the handle. The second snap-fit means 11 may be in the form of a resilient flange configured for snapping behind a first snap-fit means in form of a flange 10 on the connector.

Figure 2:
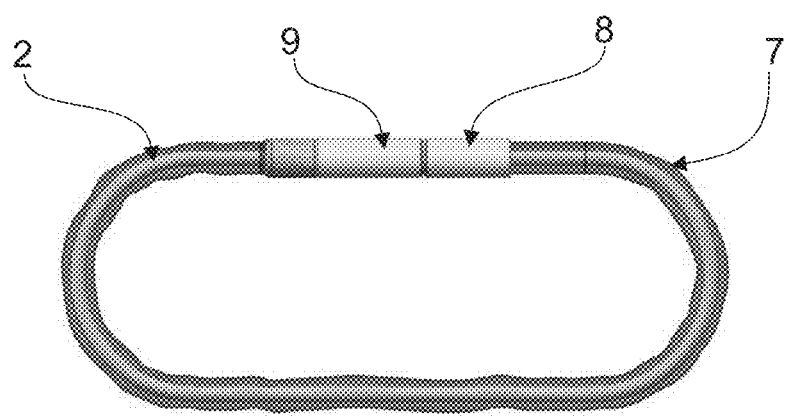
FIG. 2 illustrates a top view of an embodiment of the urinary catheter assembly in a configuration for storing.
Figure 3:
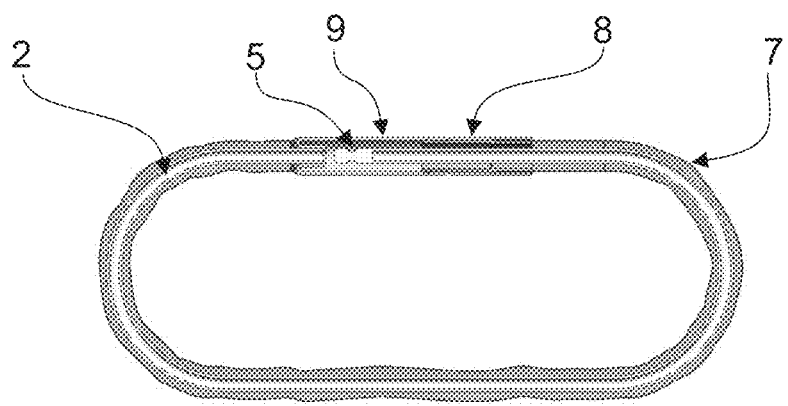
FIG. 3 illustrates a cross-sectional view of an embodiment of the urinary catheter assembly in a configuration for storing.

FIG. 2 illustrates a top view and FIG. 3 illustrates a cross-sectional view of an embodiment of a urinary catheter assembly 1 in a storage condition. When stored, the connector 9 is attached to the handle 8 and the catheter 2 is thus completely enclosed or encapsulated in the cavity provided by the sleeve 7, connector 9 and handle 8.

Figure 4:
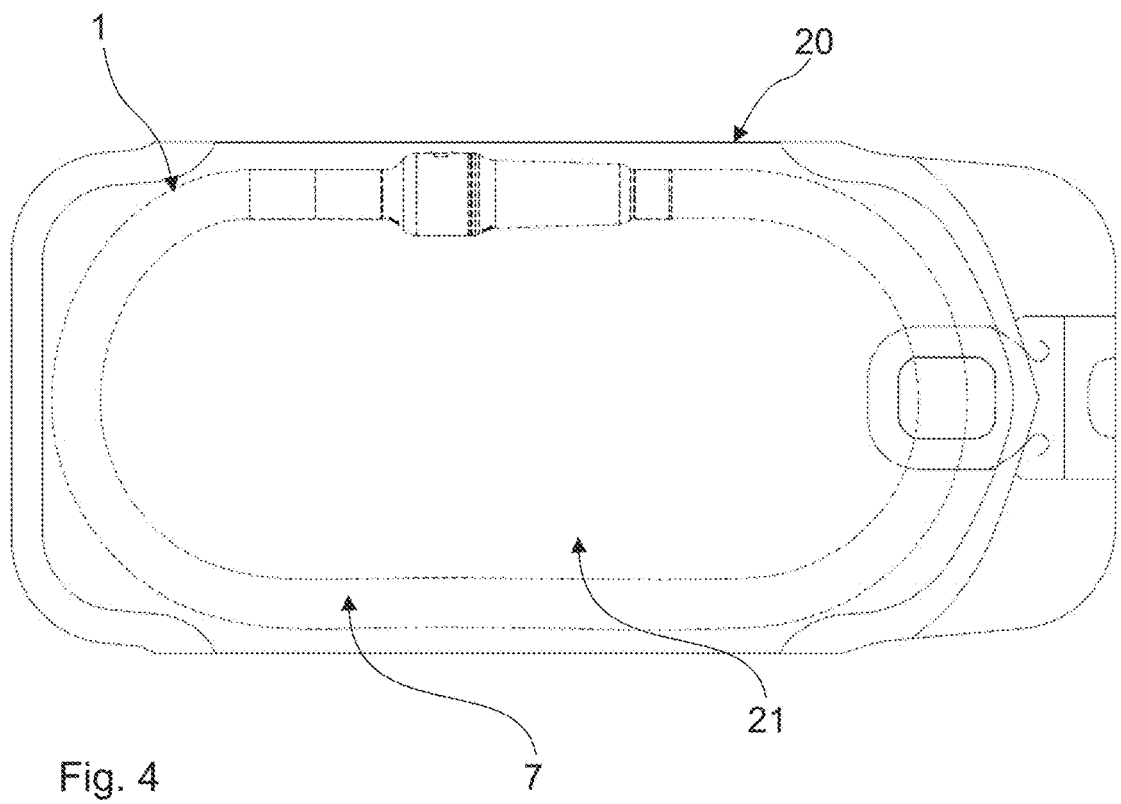
FIG. 4 illustrates an embodiment of a urinary catheter assembly stored in a storage package.

FIG. 4 illustrates an embodiment of a urinary catheter assembly 1 packed and stored in a storage package 20. In this embodiment, the storage package 20 is made of foil material welded along the edges to provide an enclosure 21 in which, the urinary catheter (not visible) including the sleeve 7 is stored during storage.

Figure 5:
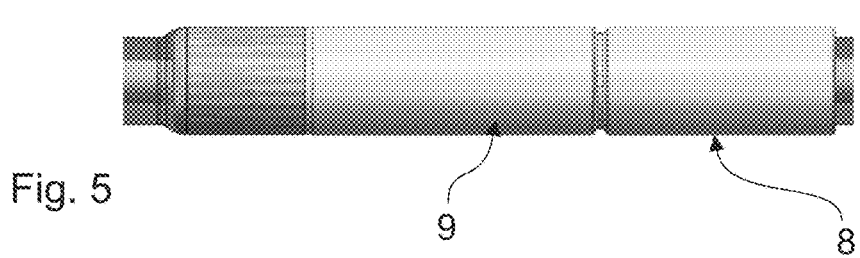
FIG. 5 illustrates a side view of a detail of an embodiment of the attachment between the handle and the connector in the storage condition.
Figure 6:
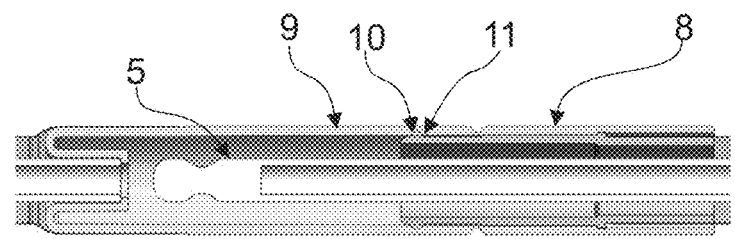
FIG. 6 illustrates a cross-sectional view of a detail of an embodiment of the attachment between the handle and the connector in the attached configuration.
Figure 7:
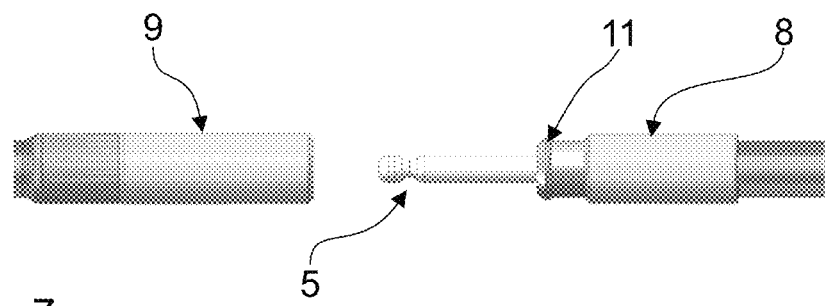
FIG. 7 illustrates a side view of a detail of an embodiment of the handle and the connector in the un-attached configuration.
Figure 8:
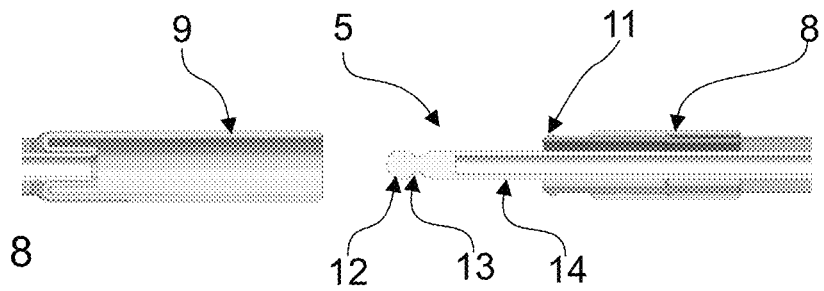
FIG. 8 illustrates a cross-sectional view of a detail of an embodiment of the attachment between the handle and the connector in the un-attached configuration.

FIGS. 5 to 8 illustrate an embodiment of a detail of the attachment between the connector 9 and the handle 8. FIGS. 5 and 7 illustrate perspective views of the attachment in an attached configuration and an un-attached configuration, respectively. FIGS. 6 and 8 illustrate cross-sectional views of the attachment in an attached configuration and in an un-attached configuration, respectively.

FIGS. 5 and 6 illustrate how the handle 8 and connector 9 are attached to each other to provide a closed connection and provide a storage cavity for the tip portion 5. FIG. 5 illustrates a view of the closed connection as seen from outside and FIG. 6 illustrates a cross-sectional view of the closed connection. The first and second snap-fit means 10 and 11 are also illustrated in FIG. 6.

FIGS. 7 and 8 illustrate the handle 8 and the connector 9 in an un-attached configuration. In FIG. 7, the handle 8 and the connector 9 are illustrated in a side-view and in FIG. 8 a cross-section view is illustrated. The second snap-fit means 11 on the handle providing for the possibility of attaching the handle to the connector. FIG. 8 also illustrates a tip portion 5 in the form of a flex-tip. The flex-tip has a proximal bulb-shaped part 12 and an intermediate part 13 immediately distal of bulb where the diameter is reduced with respect to the main tubular part 14 of the catheter.

Figure 9:
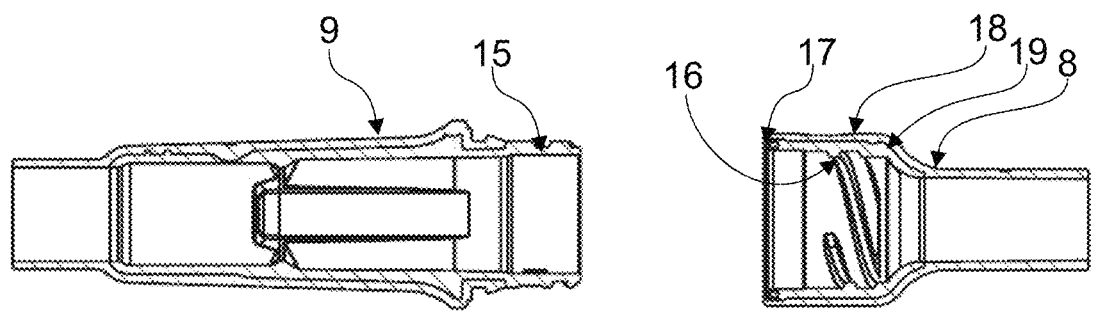
FIG. 9 illustrates a cross-sectional view of a detail of an embodiment of the attachment between the handle and the connector in the un-attached configuration.

FIG. 9 illustrates another embodiment of a connection between the handle 8 and the connector 9 in an un-attached configuration. In this embodiment, the handle and the connector are connected by a threaded coupling. The outer thread 15 is in this embodiment positioned at the connector 9 and the inner thread 16 is positioned at the handle 8. The handle 8 may be provided with a soft proximal end 17, for example made of a softer material. In the illustrated embodiment, the outer material 18 of the handle covers the handle from the distal end to the proximal end, whereas the inner material is only present at a central part of the handle. Thus, the distal end and the proximal end of the handle are unsupported by the inner material and are thus softer and more compliant.

Figure 10:
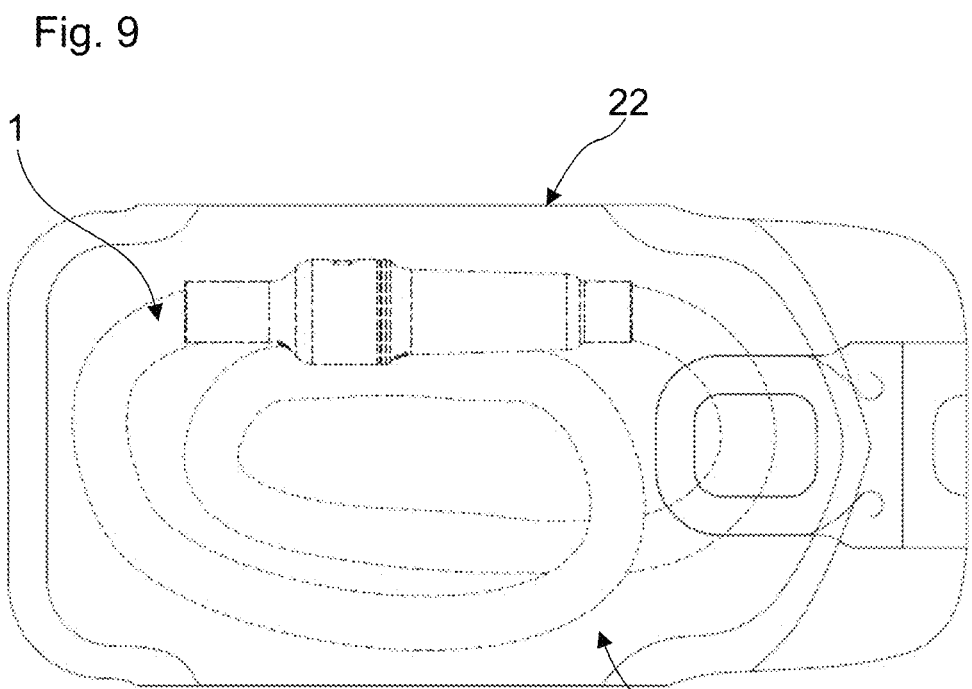
FIG. 10 illustrates a side view of an embodiment of a urinary catheter assembly in a rolled-up configuration in a storage package.
Figure 11:
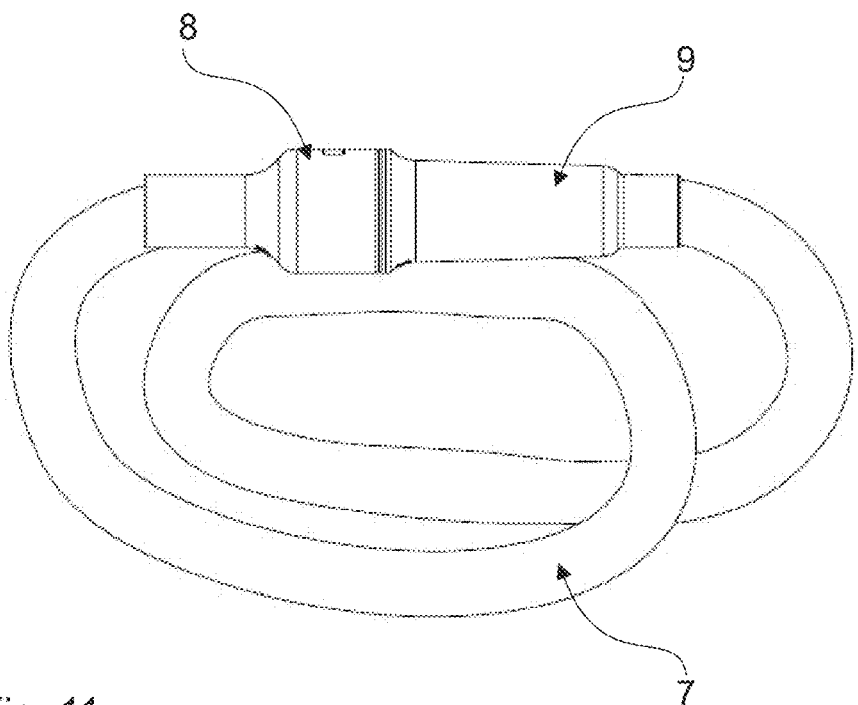
FIG. 11 illustrates a side view of an embodiment of a urinary catheter assembly in a rolled-up configuration.

FIGS. 10 and 11 illustrate an embodiment of a urinary catheter assembly 1 in a configuration, where it is rolled up in two convolutions. In FIG. 10, the urinary catheter assembly is illustrated in a storage package 22. The storage package 22 provides an enclosure 23 for the urinary catheter. FIG. 11 illustrates the urinary catheter assembly 1 in a rolled-up configuration without a storage package.

Figure 12:
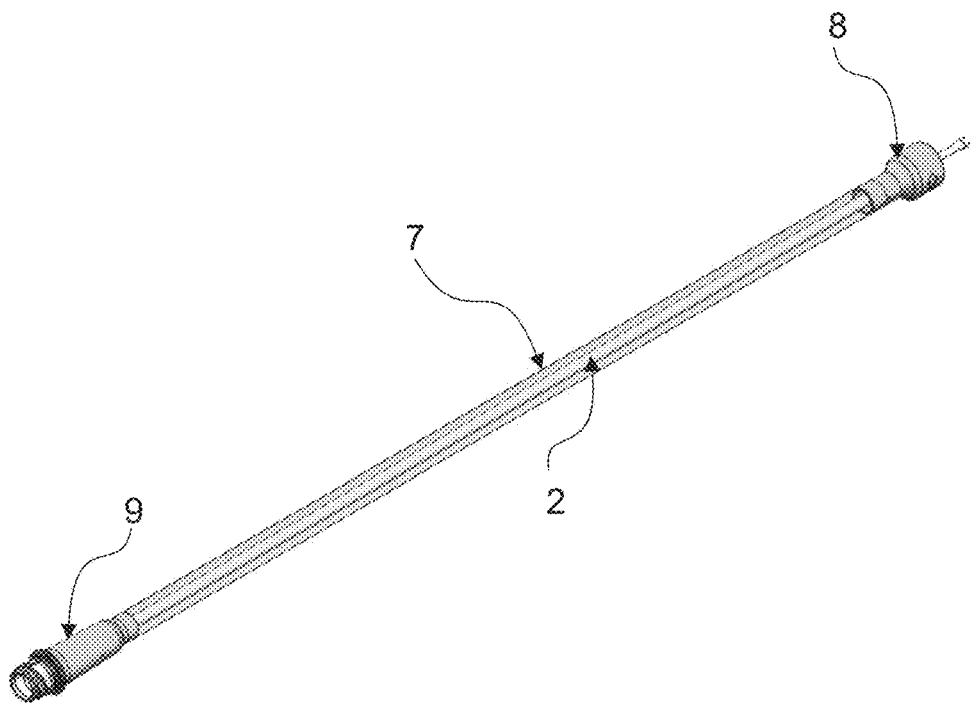
FIG. 12 illustrates a perspective view of an embodiment of a urinary catheter in a use condition.

FIG. 12 illustrates an embodiment of a urinary catheter assembly 1 when it is ready to be used with the handle 8 and connector 9 separated from each other and the catheter ready for insertion. The sleeve 7 can be seen as covering the urinary catheter 2 for a majority of the entire length.

Figure 13:
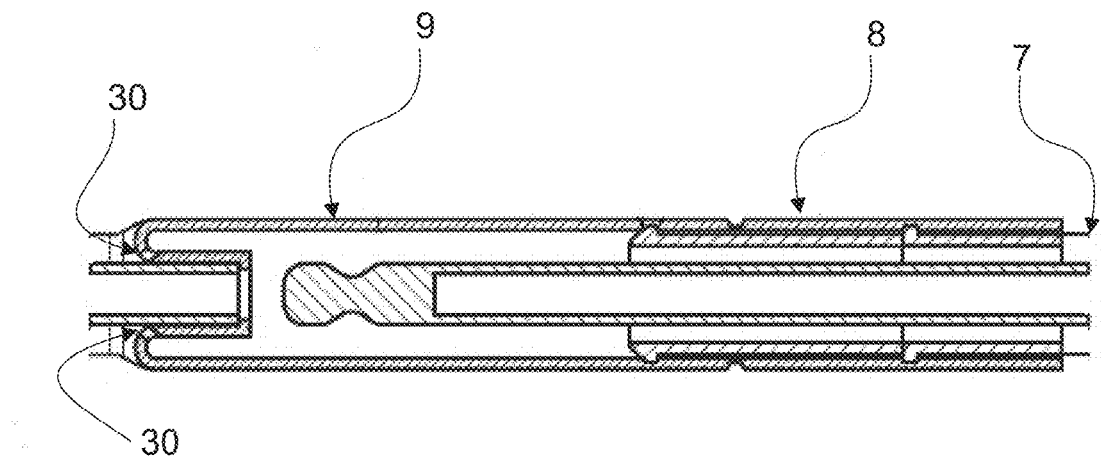
FIGS. 13 and 14 illustrate cross-sectional views of details of embodiments of a drainage structure.

The embodiment of FIG. 13 incorporates a drainage structure 30, which takes the form of one or more channels through the connector 9. It can be seen that any liquid present within the cavity formed by the connector 9, sleeve 7 and handle 8 can drain from the assembly through the connector 9, when the assembly is in the use condition or open configuration.

Figure 14:
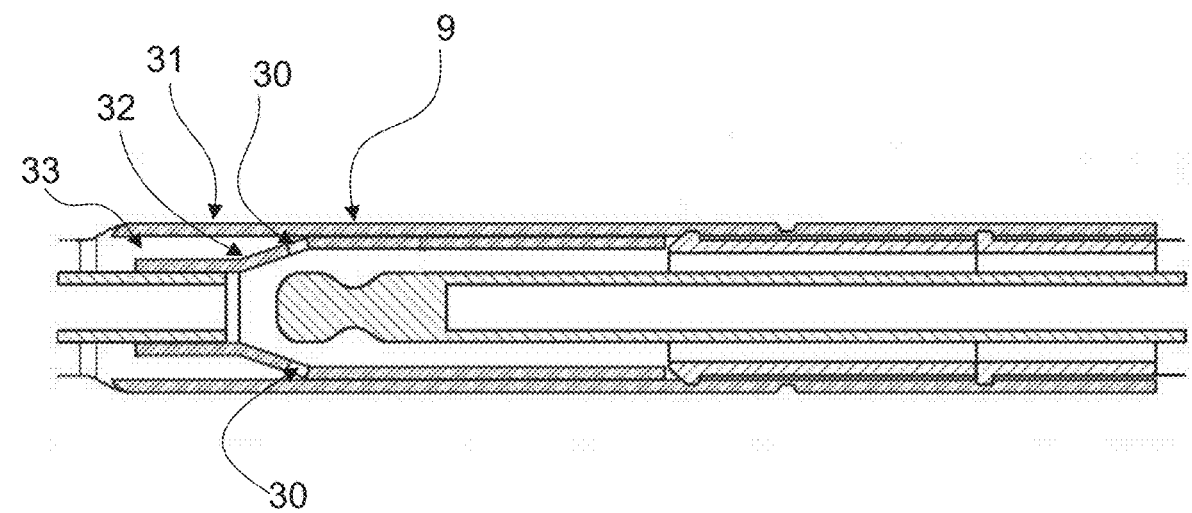

FIG. 14 illustrates a particular embodiment in which the connector 9 comprises an inner connector 31 and an outer connector 32. The inner and outer connectors (31, 32) are separated by a channel for liquid 33, wherein said drainage structure 30 is present in said inner connector 31.

The invention claimed is:

1. A urinary catheter assembly comprising:
   an intermittent urinary catheter having a distal end portion located opposite from an insertion tip formed on a proximal end portion of the intermittent urinary catheter, with an exterior surface of the intermittent urinary catheter including a hydrophilic coating;
   a handle disposed in a sliding relationship to the intermittent urinary catheter;
   a connector coupled to the distal end portion of the intermittent urinary catheter; and
   a sleeve attached to and extending between the handle and the connector;
   wherein the connector is configured to be removably attached to the handle to define a cavity formed by the handle and the connector and the sleeve, where the cavity is configured to enclose an entirety of the intermittent urinary catheter;
   a liquid inside the cavity, and the liquid is adapted to hydrate the hydrophilic coating to provide the exterior surface of the intermittent urinary with a lubricious surface;
   wherein the connector has a drain, and the drain is formed by an outer wall of the connector separated from an inner wall of the connector by a channel, and the liquid inside the cavity is adapted to flow out of the cavity through the channel when the connector is detached from the handle.

2. The urinary catheter assembly of claim 1, wherein the drain is funnel-shaped.

3. The urinary catheter assembly of claim 1, wherein the drain includes drainage holes formed in the inner wall of the connector, and the drainage holes communicate with the channel.

4. The urinary catheter assembly of claim 1, wherein the distal end portion of the intermittent urinary catheter is coupled with the inner wall of the connector.

5. The urinary catheter assembly of claim 1, wherein the outer wall and the inner wall of the connector form a double-walled connector.

6. The urinary catheter assembly of claim 1, wherein the insertion tip formed on the proximal end portion of the intermittent urinary catheter is disposed inside of the connector when the connector is attached to the handle.

7. The urinary catheter assembly of claim 1, wherein the insertion tip formed on the proximal end portion of the intermittent urinary catheter is retained inside of the connector immediately adjacent to the inner wall of the connector when the connector is attached to the handle.

8. The urinary catheter assembly of claim 1, wherein the insertion tip formed on the proximal end portion of the intermittent urinary catheter is retained inside of the connector and disposed immediately adjacent to the distal end portion of the intermittent urinary catheter when the connector is attached to the handle.

9. The urinary catheter assembly of claim 1, wherein the connector is removably attached to the handle by a threaded coupling.

10. The urinary catheter assembly of claim 1, wherein the sleeve is a liquid-tight barrier.

11. The urinary catheter assembly of claim 1, wherein the sleeve is a collapsible sleeve.

12. The urinary catheter assembly of claim 1, wherein the insertion tip includes a spherical bulb.

\* \* \* \* \*